(12) United States Patent
Morris et al.

(10) Patent No.: US 11,672,956 B2
(45) Date of Patent: Jun. 13, 2023

(54) MULTI-PURPOSE CATHETER FOR BRACHYTHERAPY AND INTRATUMORAL INJECTION

(71) Applicant: Wisconsin Alumni Research Foundation, Madison, WI (US)

(72) Inventors: Zachary Morris, Madison, WI (US); Justin Jagodinsky, Madison, WI (US); Jason Wang, Madison, WI (US); Rebecca Gillis, Shoreview, MN (US); Nur Amira Binti Mohd Razuan, Madison, WI (US); Alexis Locsin, Eden Prairie, MN (US); Jiacomo Beckman, Madison, WI (US); Tirhas G. Dempsey, Bethesda, MD (US); Hayley H. Raj, Fox Point, WI (US); Gabriella Medeiros Simas, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 521 days.

(21) Appl. No.: 16/816,857

(22) Filed: Mar. 12, 2020

(65) Prior Publication Data
US 2020/0289793 A1   Sep. 17, 2020

Related U.S. Application Data

(60) Provisional application No. 62/817,160, filed on Mar. 12, 2019.

(51) Int. Cl.
*A61M 25/06* (2006.01)
*A61N 5/10* (2006.01)
(Continued)

(52) U.S. Cl.
CPC ...... *A61M 25/0662* (2013.01); *A61M 5/1452* (2013.01); *A61M 25/007* (2013.01);
(Continued)

(58) Field of Classification Search
CPC .... A61N 5/1001–1029; A61M 25/007; A61M 2025/0004; A61M 25/00–104; A61M 2025/1043–1097
See application file for complete search history.

(56) References Cited

U.S. PATENT DOCUMENTS 6,918,869 B2    7/2005  Shaw et al.
2011/0202054 A1*  8/2011  Wang .................. A61B 18/1492
                                                                      606/41

(Continued)

OTHER PUBLICATIONS

Patel et al., Combining Brachytherapy and Immunotherapy to Achieve In Situ Tumor Vaccination: A Review of Cooperative Mechanisms and Clinical Opportunities, Brachytherapy 17 (2018) 995-1003.

*Primary Examiner* — Thaddeus B Cox
(74) *Attorney, Agent, or Firm* — Boyle Fredrickson S.C.

(57) ABSTRACT

A single treatment catheter is provided for delivery of brachytherapy radiation in combination with intratumoral injection into tumor tissue with a single skin and tumor insertion site. The catheter also enables precise delivery of anti-cancer agents, such as immunotherapy or other medical substances, to specific locations within the tumor with radiographic confirmation of the injection delivery area and location.

16 Claims, 4 Drawing Sheets

(51) Int. Cl.
  *A61M 5/145* (2006.01)
  *A61M 25/00* (2006.01)
(52) U.S. Cl.
  CPC ......... *A61N 5/1007* (2013.01); *A61N 5/1027* (2013.01); *A61M 2025/0004* (2013.01); *A61M 2025/0681* (2013.01); *A61M 2205/051* (2013.01); *A61N 2005/1024* (2013.01)

(56) References Cited

U.S. PATENT DOCUMENTS

| | | | | |
|---|---|---|---|---|
| 2014/0257244 A1* | 9/2014 | Johnston | ........... | A61M 25/0017 604/266 |
| 2014/0276602 A1* | 9/2014 | Bonnette | .......... | A61B 17/32037 604/151 |
| 2015/0088051 A1* | 3/2015 | Ragg | ..................... | A61K 9/122 514/723 |

* cited by examiner

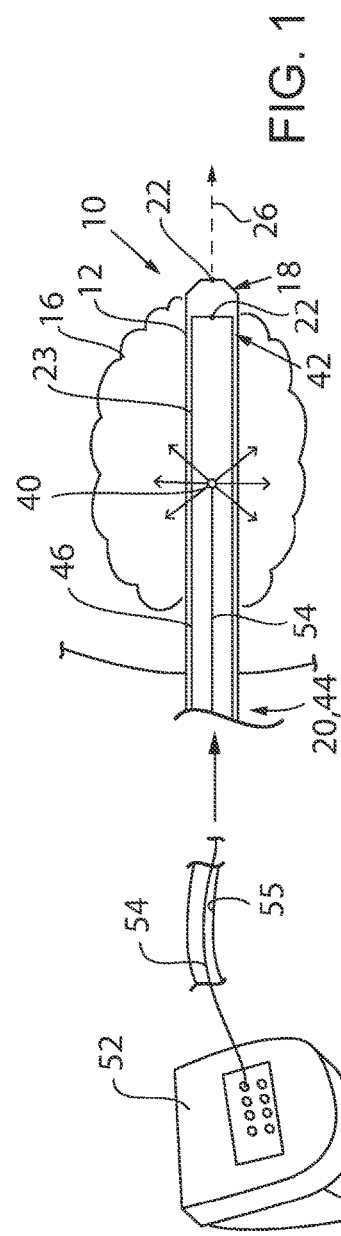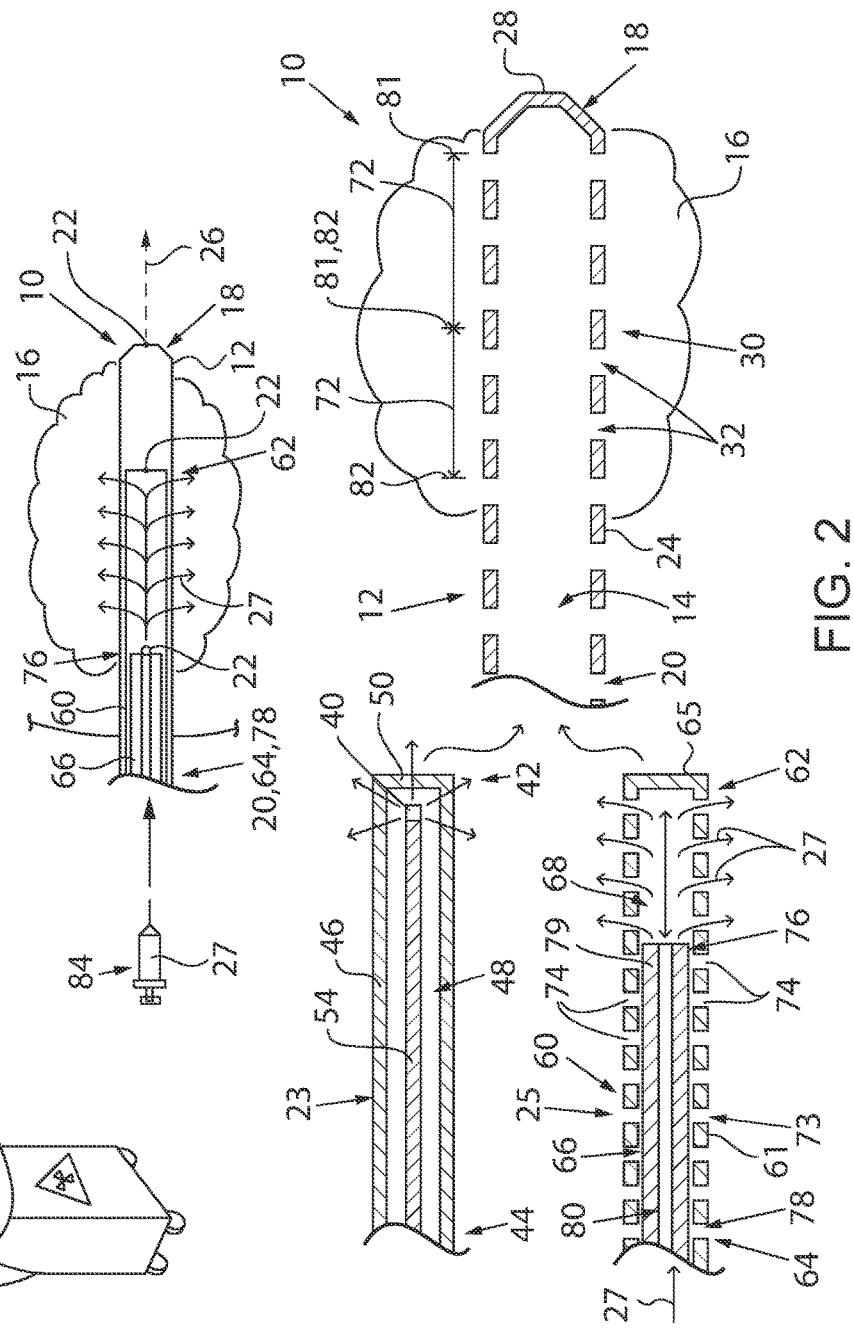

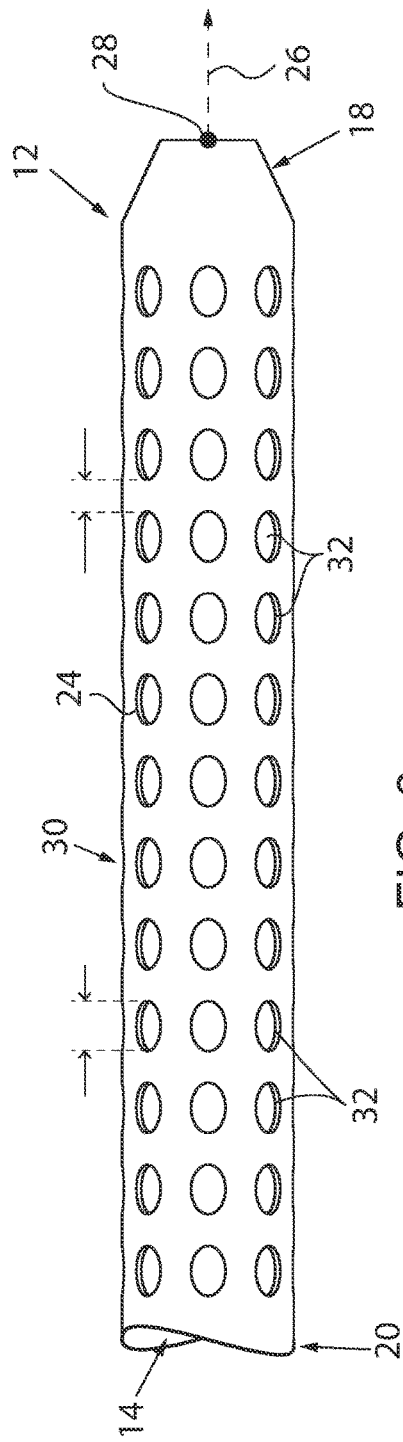
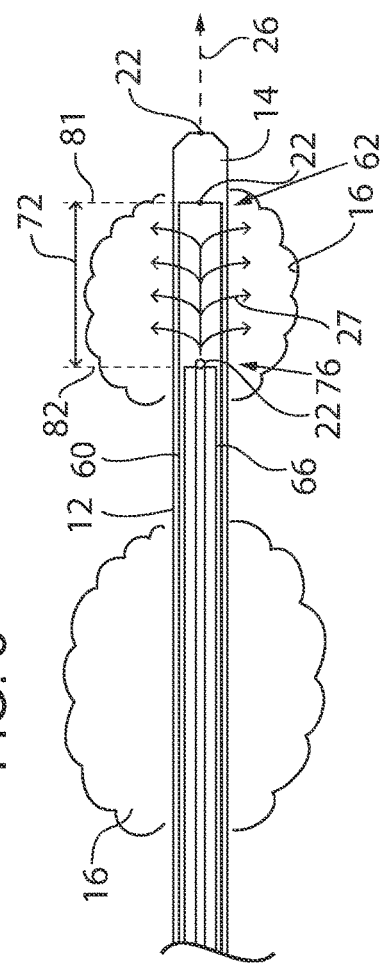
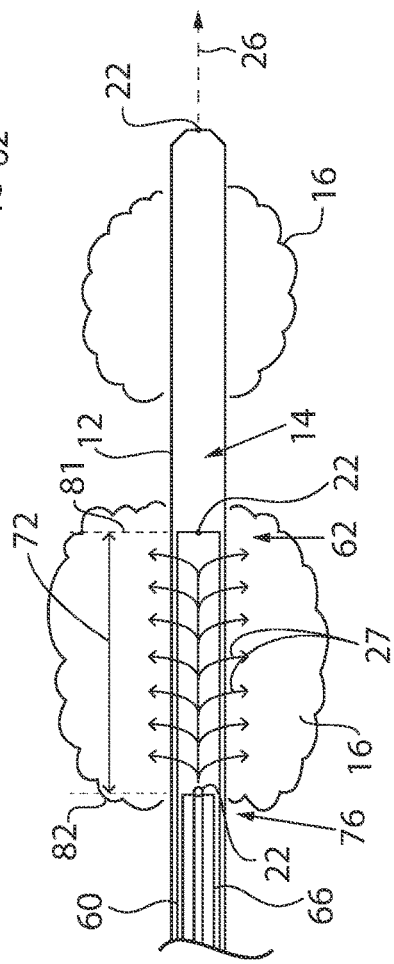
FIG. 3
FIG. 4

MULTI-PURPOSE CATHETER FOR BRACHYTHERAPY AND INTRATUMORAL INJECTION

CROSS REFERENCE TO RELATED APPLICATION

This application claims the benefit of U.S. provisional application 62/817,160, filed Mar. 12, 2019, and hereby incorporated by reference.

STATEMENT REGARDING FEDERALLY SPONSORED RESEARCH OR DEVELOPMENT

--

BACKGROUND OF THE INVENTION

The present invention relates to a delivery catheter, and in particular, to a multipurpose delivery catheter that can be used to deliver both brachytherapy and intra/peri-tumor injection of a liquid solution at a targeted tumor site, including but not limited to injection of immunotherapy(s), chemotherapy(s), cellular therapies, viral therapies, or pathology or radiology markers (e.g. tattoo ink or contrast agents).

One of the hallmarks of tumorigenesis is the ability of cancer cells to suppress or circumvent the host immune system. The mechanisms by which cancer cells evade both innate and adaptive immunity are complex and result, at least in part, from the selective effects of immuno-editing.

Tumor vaccines are a class of treatments that seek to activate a patient's immune system to specifically recognize and attack cancer cells. Vaccine approaches include dendritic cell vaccines, viral vaccines, nucleic acid vaccines, whole tumor cell vaccines, and protein/peptide vaccines.

As immunotherapies such as tumor vaccines continue to emerge as a standard component of treatment for a variety of cancers, the need for testing immunotherapies in combination with other standard cancer therapies grows. Immunotherapies may be preferred as a method of treatment for the following reasons: (1) Some chemotherapies or other cancer treatments can be safe if locally delivered by not safe or poorly tolerated if given systemically (e.g. IL2, oncolytic viruses, various cytotoxic chemotherapies). (2) Some treatments can be effective once in a tumor but are not effectively conveyed to the tumor by systemic (oral or IV) routes and delivering these to the tumor directly can potentially overcome this limitation (e.g. certain chemotherapies, cell therapies like CAR-T cells). (3) Brachytherapy delivers radiation dose from a radioactive seed, but the position of these seeds is poorly defined in the tissue. For some applications it may be important to locate these dwell positions in tissue after brachytherapy (e.g. at time of surgery). Delivering local injection of ink or a contrast agent could enable this and other pathology or radiology-based applications/studies in patents getting brachytherapy.

SUMMARY OF THE INVENTION

The present inventors have recognized that combinations of immunotherapies have resulted in increased risk of systemic toxicities. One approach to limit this systemic toxicity, while capitalizing on the potential for synergistic immunotherapy combinations, is to deliver immunotherapies directly into a tumor via intratumoral injection. Because the adaptive immune system is already designed to generate systemic responses, these therapies may be particularly well suited to local delivery in a single tumor where high local concentrations can be achieved at doses that are relatively low compared with those needed to achieve efficacy with systemic delivery.

The present inventors have also recognized that systemically toxic chemotherapies or molecularly targeted therapies may not be safe to deliver to the whole body but may be safely delivered directly to a tumor where they may enhance response to brachytherapy. One potential approach to improving the response to cancer immunotherapies is to combine such immunotherapies with radiotherapy. The mechanisms by which radiation may interact with the tumor immune microenvironment at a targeted site include (1) temporary local eradication of radiation-sensitive immune lineages including suppressor and effector lymphocytes, (2) local release of inflammatory cytokines and damage-associated molecular patterns resulting in local effects on endothelial cell expression of adhesion receptors, immune cell trafficking, and immune cell activation, (3) immunogenic tumor cell death and release of tumor-specific antigens, and (4) induction of phenotypic changes in the expression of immune susceptibility markers on tumor cells surviving radiation. Because of these effects, radiation may enhance dendritic cell maturation, antigen cross-presentation, and diversification of antitumor T cell responses. Therefore, radiation may elicit an "in situ tumor vaccination" effect, converting a patient's own tumor into a nidus for presentation of tumor-specific antigens in a way that will stimulate and diversify the antitumor immune response.

The present inventors have also recognized that current approaches to radiotherapy, such as utilizing external beam radiation therapy (EBRT), requires radiation to pass through considerable volumes of normal tissue to reach targeted tumor volumes and may cause off-target effects to radio sensitive lymphoid immune cells (e.g., naive T cells) in normal tissue that receive low-dose radiation, leading to long-term lymphopenia in some cases. Because brachytherapy radiation requires the insertion of a radiation source into the tumor tissue, sparing normal tissue and pertinent lymphoid organs from off-target radiation exposure, this mode of radiation may be particularly amenable for combined modality approaches that require injection of immune modulating agents directly into tumor tissue.

The present invention provides a single treatment catheter for delivery of both brachytherapy radiation in combination with intratumoral injection into tumor tissue with a single catheter insertion. The catheter also enables precise delivery of anti-cancer agents, such as immunotherapy or other medical substances, to specific sites within the tumor with radiographic and potentially pathologic confirmation of the injection delivery area and location.

Specifically, then, in one embodiment, the invention provides a catheter assembly having an outer tube having a wall surrounding a central lumen extending along an axis and including one or more exit ports distributed along its length extending through the wall and having an open proximal end. An inner tube is sized to be received within the outer tube along the axis having a wall surrounding a central lumen extending along the axis and slidably receivable within the central lumen of the outer tube along the axis and having a closed distal end and having one or more exit ports extending through the wall and communicating with the exit ports of the outer tube to allow fluid flow from the central lumen of the inner tube through the exit ports of the outer tube at a range of relative positions along the axis. An inner plunger is slidably receivable within the central lumen of the inner tube along the axis, the plunger interfacing with the inner tube to promote fluid flow out of the exit ports of the inner tube and outer tube by translating the plunger along the axis.

It is thus a feature of at least one embodiment of the invention to localize the delivery of immunotherapy drugs into a tumor by exit holes aligning with the exit holes of the outer tube and an inner tube having a plunger to expel the fluid from the inner tube.

The exit ports of the outer tube and inner tube may be distributed about a circumference of the tubes.

It is thus a feature of at least one embodiment of the invention to provide a catheter providing radial delivery of immunotherapy drugs within or around a tumor site to provide improved dispersion of drugs in a three-dimensional area of the surrounding tumor.

The outer tube and inner tube may fit to restrict fluid flow axially between the outer tube and the inner tube. The outer tube and inner tube may provide a liquid tight seal against fluid flow axially between the outer tube and the inner tube.

It is thus a feature of at least one embodiment of the invention to provide a catheter that directs fluid flow outward through the radial exit ports while preventing backflow of fluids through the catheter resulting in fluid waste.

The exit ports may be circular. The spacing between the exit ports about the axis may be less than a diameter of each port. The exit ports may be separated by a distance that is less than 5 mm apart about the axis.

It is thus a feature of at least one embodiment of the invention to provide a catheter that encourages overlap or alignment of the respective exit ports of the outer tube and the inner tube to promote fluid flow outward through the exit ports against the resistance of the surrounding tissue.

The exit ports may be separated by a distance that is less than 10 mm along the axis.

It is thus a feature of at least one embodiment of the invention to provide a catheter that promotes the outflow of fluid circumferentially at longitudinal positions with approximately equal radial fluid distribution and focus delivery at multiple targeted tumor sites and tissue depths.

The outer tube and inner tube may be substantially cylindrical. The cylindrical tubes may be circular or oval in cross section.

It is thus a feature of at least one embodiment of the invention to facilitate insertion of the outer and inner tube of the catheter into the body and body cavities while minimizing disturbance to the surrounding tissues.

The outer tube and inner tube may be flexible. The outer tube and inner tube may be constructed of a polytetrafluoroethylene fluoropolymer.

It is thus a feature of at least one embodiment of the invention to allow the outer tube of the catheter to be flexibly maneuvered through the body to its desired position and the inner tube of the catheter to be easily inserted through the outer tube without resistance.

The outer tube may have a closed distal end converging to a tapered point.

It is thus a feature of at least one embodiment of the invention to facilitate penetration of the outer tube of the catheter through body tissue to the tumor site.

The assembly may further include at least one radiopaque marker indicating a position of the closed distal end of the inner tube and at least one radiopaque marker indicating a position of the distal end of the inner plunger with respect to the inner tube.

It is thus a feature of at least one embodiment of the invention to utilize image guidance already used for placement of the outer catheter to also visualize precise alignment of the fluid delivery location of the catheter.

The assembly may further include a brachytherapy insertion catheter fitting within the outer tube. The lumen of the brachytherapy insertion catheter may be sized to receive radiotherapy seeds guided therealong.

It is thus a feature of at least one embodiment of the invention to provide co-location of radiotherapy and immunotherapy drugs using a single outer tube catheter.

In an alternative embodiment, the present invention provides a method of performing cancer therapies including the steps of: inserting into a targeted tumor site an outer tube having a wall surrounding a central lumen extending along an axis and including one or more exit ports distributed along its length extending through the wall and having an open proximal end; inserting an inner tube within the outer tube along the axis having a wall surrounding a central lumen extending along the axis and slidably receivable within the central lumen of the outer tube along the axis and having a closed distal end and having one or more exit ports communicating with the exit ports of the outer tube to allow fluid flow from the central lumen of the inner tube through the exit ports of the outer tube at a range of relative positions along the axis; inserting an inner plunger within the central lumen of the inner tube along the axis to receive a fluid, the plunger interfacing with the inner tube to promote fluid flow into and out of the exit ports of the inner tube; and pressing on the inner plunger to inject an immunotherapy or other solution out of the exit ports of the inner tube and through the exit ports of the outer tube.

The method may further include the steps of adjusting a position of the closed distal end of the inner tube with respect to the outer tube.

It is thus a feature of at least one embodiment of the invention to perform more precise intratumoral injections by setting an exact delivery location along the catheter.

The method may further include the steps of inserting a brachytherapy insertion catheter fitting within the outer tube and guiding a radioactive seed through a lumen of the brachytherapy insertion catheter. The outer tube may remain in substantially the same position in the body during the steps.

It is thus a feature of at least one embodiment of the invention to combine multiple cancer therapies using a single catheter placement in the patient and utilizing the heterogeneity of radiation dose from brachytherapy to provide a synergistic response.

These particular objects and advantages may apply to only some embodiments falling within the claims and thus do not define the scope of the invention.

BRIEF DESCRIPTION OF THE DRAWINGS

FIG. 1 is a schematic of a catheter assembly constructed according to the present invention showing a needle outer tube and two inner tubes being inserted into a tumor site for delivery of brachytherapy and intratumoral injection respectively;

FIG. 2 is a cross-sectional view of a brachytherapy insertion catheter of the catheter assembly of FIG. 1 insertable into the needle outer tube, and an intratumoral injection catheter of the catheter assembly of FIG. 1 insertable into the needle outer tube and further holding a plunger to provide precise delivery of an immunotherapy or other medical substance through exit ports of the intratumoral injection catheter and the needle outer tube;

FIG. 3 is a perspective view of one embodiment of the needle outer tube of the catheter assembly;

FIG. 4 is a schematic of the catheter assembly being inserted into a tumor site where a smaller and deeper tumor is treated followed by a larger and shallower tumor by precise positioning of the needle outer tube, the intratumoral injection catheter, and the plunger with respect to the tumor site;

DETAILED DESCRIPTION OF THE PREFERRED EMBODIMENT

Figure 5:
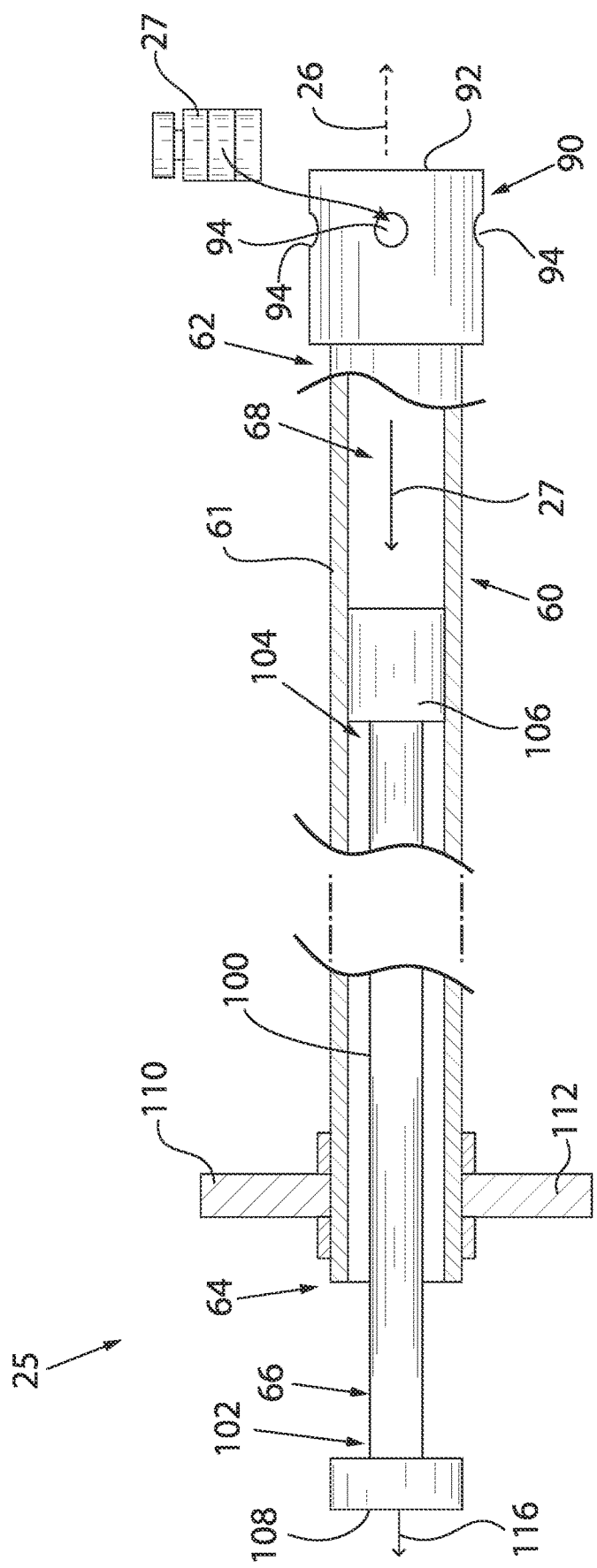
FIG. 5 is a partial cross-sectional exploded view of a catheter assembly an alternative embodiment of the present invention showing an intratumoral injection catheter having a plunger being pulled outwardly along the inner tube to fill the intratumoral injection catheter with medical fluid through its inlet/outlet ports.

Referring now to FIGS. 1 and 2, a single treatment catheter assembly 10 of the present invention may provide a needle or cannula outer catheter defined by an outer tube 12 having an inner lumen 14 and penetrating through skin, for example, through an orifice or incision in the skin, and extending through normal tissue to a tumor site 16. The tumor site 16 may contain a tumor or multiple tumors, each tumor generally extending 1 to 15 cm in length and width within the body. The outer tube 12 may include a distal end 18 inserted into or proximate the tumor site 16 and extending outward to an open proximal end 20 positioned outside of the patient's body.

The placement of the outer tube 12 within the body may be assisted by a stiffening wire or stylet inserted through the inner lumen 14 of the outer tube 12 and providing rigidity to the outer tube 12 as the outer tube 12 is introduced into the body. The stylet may be pulled through and removed once the outer tube 12 is positioned in place. The stylet may be made of metal, for example, stainless steel or relatively stiff plastic or other stiffening material as known in the art.

As is generally understood, the placement of the outer tube 12 within the body may be assisted by a guiding member such as a guidewire and image guidance known in the art. Image guidance may come in the form of an alignment indicator such as radiopaque markers 22 at the distal end, external depth markings at the proximal end, and the like, located on the guiding member and/or outer tube 12 that can be utilized by the medical professional in locating the position of the distal end of the guiding member and/or outer tube 12 within the body relative to the tumor site 16. In one embodiment, the radiopaque markers 22 may be bands of material such as iridium, platinum, or other suitable material, wrapped around the outer tube 12 and located by the medical professional using an image guidance system such as fluoroscopy, MRI, CT scan, x-ray, ultrasound, and the like to determine the position of the distal end 18 of the catheter assembly 10 within the body relative to the tumor site 16. For example, a radiopaque marker 22 may be located at the distal end 18 of the outer tube 12 or multiple radiopaque markers 22 may be spaced along a length of the outer tube 12 at known increments to provide visualization and confirmation of the position of the distal end 18 of the outer tube 12 within the body with respect to the tumor site 16.

The outer tube 12 may then sequentially receive an inner brachytherapy insertion catheter 23 for delivery of a radiation source followed by an inner intratumoral injection catheter 25 for delivery of an immunotherapy or other medical substance 27 without the need to move or remove the outer tube 12 from its initial placement within the body, as will be further discussed in detail below.

Referring now also to FIG. 3, the outer tube 12 may be an elongated circular cylindrical tube extending between the distal end 18 and the proximal end 20 along an axis 26 and having a length of at least 10 centimeters and at least 26 centimeters and approximately 26 centimeters to 1 meter long. The outer tube 12 may also be oval in cross section.

The outer tube 12 may include an outer tube wall 24 surrounding an inner lumen 14 having a generally constant inner and outer diameter, the outer diameter of the outer tube 12 generally ranging from 1.5 mm to 2.5 mm, for example, between 5 French and 7 French. The thickness of the outer tube wall 24 may be approximately 0.1 mm to 0.5 mm. The outer tube wall 24 of the outer tube 12 may be constructed of a thermoplastic having temperature resistance, is chemically inert, has a low coefficient of friction, and good biocompatibility. The material may be a fluoropolymer such as polytetrafluoroethylene (PTFE). The flexible material of the outer tube 12 allows the outer tube 12 to be easily inserted through tissue to a desired location.

The distal end 18 of the outer tube wall 24 extending into the tumor site 16 may converge to a pointed tip 28 tapering inwardly as the outer tube wall 24 moves toward the distal end 18 and may be blunted by a plane perpendicular to the axis 26 at its tip. The tip 28 may be closed along axis 26. In some embodiments, the tip 28 may be open along axis 26, for example, to allow the catheter assembly 10 to be fed over a guidewire during placement.

A delivery portion 30 of the outer tube 12 expected to be inserted through or proximate to the tumor site 16, for example, extending at least 15 cm and at least 30 cm from the distal end 18 toward the proximal end 20, may include one or more exit ports 32 extending through the outer tube wall 24, and spaced in equal separation about a circumference of the outer tube 12, and spaced in generally equal separation along a length of the outer tube 12 along axis 26.

The exit ports 32 may be elongated slots taking a generally rectangular, circular, or oblong shape although other shapes are also contemplated. The exit ports 32 may be less than 5 mm wide and less than 3 mm wide and approximately 0.5 mm to 5 mm wide extending about axis 26, and less than 20 mm long and less than 10 mm long and approximately 5 mm to 10 mm long extending along axis 26. The length of the exit ports 32 may be about 1 to 5 times its width.

The exit ports 32 may be separated by a distance that is less than 5 mm apart and less than 3 mm apart and approximately 0.5 mm to 5 mm apart about axis 26, and less than 20 mm apart and less than 5 mm apart and less than 3 mm apart and approximately 0.5 mm to 5 mm apart along axis 26. The longitudinal spacing between exit ports 32 along axis 26 is less than a length of the exit ports 32. In one embodiment, the exit ports 32 may include at least one and between one and eight exit ports 32 spaced equally about the axis 26 to form a ring of exit ports 32, and at least ten rings of exit ports 32 spaced along axis 26 for a total of at least twenty or at least fifty or at least one hundred exit ports 32 within the delivery portion 30 of the outer tube 12. The number and arrangement of the exit ports 32 may vary while still allowing a fluid to be expelled therethrough the exit ports 32 as further described below.

Referring again to FIGS. 1 and 2, after the delivery portion 30 of the outer tube 12 is positioned close to or within the tumor site 16, and assisted by image guidance such as radiopaque markers 22 positioned at the distal end 18 or along a length of the outer tube 12 at predetermined increments, the inner brachytherapy insertion catheter 23 may be installed through the inner lumen 14 of the outer tube 12 to introduce a radioactive source or seed 40 fed into the catheter assembly 10. The radioactive seed 40 may be for example a $^{192}$Ir source transported through the catheter assembly 10 to the target location.

The inner brachytherapy insertion catheter 23 may be an elongated circular cylindrical tube extending between a distal end 42 and a proximal end 44 and having a typical length of 26 centimeters and at least 10 centimeters and at least 25 centimeters and approximately 25 centimeters to 1 meter long. The inner brachytherapy insertion catheter 23 may also be oval in cross section.

The inner brachytherapy insertion catheter 23 may include an outer wall 46 surrounding an inner lumen 48 having a generally constant inner and outer diameter. The diameter of the inner brachytherapy insertion catheter 23 may generally range from 1.5 mm to 2.5 mm for example between 5 French and 7 French and is able to be inserted within the lumen of the outer tube 12. The thickness of the inner brachytherapy insertion catheter 23 may be approximately 0.1 mm to 0.5 mm. The outer wall 46 of the inner brachytherapy insertion catheter 23 may be constructed of a thermoplastic having temperature resistance, is chemically inert, has a low coefficient of friction, and good biocompatibility. The material may be a fluoropolymer such as polytetrafluoroethylene (PTFE). The inner brachytherapy insertion catheter 23 may be a flexible material to allow the outer wall 46 to be easily inserted into the outer tube 12. The inner brachytherapy insertion catheter 23 and outer tube 12 may be radiation resistant and able to withstand a maximum exposure of $1.7 \times 10^4$ rads for twenty to thirty minutes.

The distal end 42 of the outer wall 46 may be closed by an end wall 50 extending perpendicular to the axis 26 preventing further extension of the radioactive seed 40 past the distal end 42 of the inner brachytherapy insertion catheter 23. The distal end 42 of the outer wall 46 may also converge to a pointed tip.

The inner brachytherapy insertion catheter 23 may be inserted through the inner lumen 14 of the outer tube 12 until the distal end 42 abuts the distal end 18 or is proximate the distal end 18 of the outer tube 12 (for example, stopped by the inwardly tapering wall of the blunt tip 28), or the distal end 42 may be predeterminately spaced from the distal end 18 of the outer tube 12 depending on the location of the tumor with respect to the distal end 18 of the outer tube 12. The position of the inner brachytherapy insertion catheter 23 within the outer tube 12 may be assisted by image guidance such as radiopaque markers 22 positioned at the distal end 42 of the inner brachytherapy insertion catheter 23 and along a length of the inner brachytherapy insertion catheter 23.

The proximal end 44 is connected to a computer-controlled brachytherapy remote afterloader 52 sending a wire 54 carrying the radioactive seed 40 via brachytherapy transfer tube 55 to the inner brachytherapy insertion catheter 23. The wire 54 travels from the open proximal end 44 to distal end 42 of the inner brachytherapy insertion catheter 23 along its inner lumen 48 until the radioactive seed 40 is positioned in the inner brachytherapy insertion catheter 23 at a desired location with respect to the tumor site 16 typically within the tumor or immediately adjacent to the tumor. The computer-controlled brachytherapy remote afterloader 52 may be of the types manufactured by Varian, Best, Oncentra, Accuray, and Elekta. The inner brachytherapy insertion catheter 23 may be of the type manufactured by Varian, Best, Oncentra, Accuray, and Elekta.

Radiation may be provided at lower and higher dose rates depending on the activity of the radioactive seed 40 and the time it remains in the body as known in the art. In one embodiment, high-dose rate brachytherapy delivers a desired dose of radiation by keeping the radioactive seed 40 at designated positions along the inner brachytherapy insertion catheter 23 for varying amounts of time. For example, as illustrated by FIG. 2, the radioactive seed 40 may be positioned at a first depth location within the tumor site 16 for a first designated amount of time and then moved to a second depth location within the tumor site 16 for a second designated amount of time. The amount of time the radioactive seed 40 spends in any one position is generally for a few seconds to 20 minutes with the overall treatment time at the tumor site 16 being generally about 20 seconds to 20 minutes. The radioactive seed 40 is then withdrawn from the tumor site 16 by being withdrawn from the inner brachytherapy insertion catheter 23, through the brachytherapy transfer tube 55 and back into the remote afterloader 52, so that the radioactive seed 40 does not remain in the body after treatment is complete.

After the radiation therapy is complete, the inner brachytherapy insertion catheter 23 is removed from the outer tube 12 and replaced by an inner intratumoral injection catheter 25 inserted into the inner lumen 14 of the outer tube 12 in a similar manner to further introduce an immunotherapy or other medical substance 27 through the catheter assembly 10. The immunotherapy or other medical substance 27 may be a tumor vaccine such as dendritic cell vaccines, viral vaccines, nucleic acid vaccines, whole tumor cell vaccines, protein/peptide vaccines, immune adjuvant, oncolytic virus, therapeutic antibody, small molecule drug, or chemotherapy known in the art.

The inner intratumoral injection catheter 25 may include an elongated circular cylindrical inner tube 60 extending between a distal end 62 and a proximal end 64 and having a length of at least 10 centimeters and at least 26 centimeters and approximately 26 centimeters to 1 meter long, and supporting therein an inner plunger 66 receiving the immunotherapy or other medical substance 27. The cylindrical inner tube 60 may also be oval in cross section.

The inner tube 60 may include an inner tube wall 61 surrounding an inner lumen 68 having a generally constant inner and outer diameter, the outer diameter closely matching the inner diameter of the outer tube 12 to restrict fluid flow axially between the outer tube 12 and the inner tube 60. In this respect, the outer diameter of the inner tube 60 of the inner intratumoral injection catheter 25 may generally range from 1.5 mm to 2.5 mm for example between 5 French and 7 French and able to be inserted within the lumen of the outer tube 12. The thickness of the inner tube wall 61 may be approximately 0.1 mm to 0.5 mm. The inner tube wall 61 may be constructed of a thermoplastic having high temperature resistance, is chemically inert, has a low coefficient of friction, and good biocompatibility. The material may be a fluoropolymer such as polytetrafluoroethylene (PTFE). The inner tube wall 61 may be a flexible material to allow the inner tube 60 to be easily inserted into and through the outer tube 12.

The distal end 62 of the inner tube 60 may be closed by an end wall 65 extending perpendicular to the axis 26 preventing fluid flow past the distal end 62 of the inner tube 60. The distal end 62 of the inner tube 60 may include a radiopaque marker 22 allowing the medical professional to position the distal end 62 of the inner tube 60 of the inner intratumoral injection catheter 25 within the outer tube 12 to a desired location.

A delivery portion 73 of the inner tube 60, generally corresponding to the delivery portion 30 of the outer tube 12, expected to be inserted through or proximate to the tumor site 16, for example, extending at least 15 cm and at least 30 cm from the distal end 62 toward the proximal end 64, may include one or more exit ports 74 extending through the inner tube wall 61 similar to the exit ports 32 of the outer tube 12. The exit ports 74 may be spaced in equal separation around a circumference of the inner tube 60, and spaced in generally equal separation along a length of the inner tube 60 along the axis 26.

The exit ports 74 may be elongated slots taking a generally rectangular, circular, or oblong shape although other shapes are contemplated. The exit ports 74 may be less than 5 mm wide and less than 3 mm wide and approximately 0.5 mm to 5 mm wide extending about axis 26, and less than 20 mm long and less than 10 mm long and approximately 5 mm to 10 mm long extending along axis 26. The length of the exit ports 32 may be about 1 to 5 times its width.

The exit ports 74 may be separated by a distance that is less than 5 mm apart and less than 3 mm apart and approximately 0.5 mm to 5 mm apart about a circumference of the inner tube 60, and less than 20 mm apart and less than 5 mm apart and less than 3 mm apart and approximately 0.5 mm to 5 mm apart along axis 26. The longitudinal spacing between exit ports 74 along axis 26 is less than a length of the exit ports 74. In one embodiment, the exit ports 74 may include at least one and between one and eight exit ports 74 spaced equally about the axis 26 to form a ring of exit ports 74, and at least ten rings of exit ports 74 spaced along axis 26 for a total of at least twenty or at least fifty or at least one hundred exit ports 74 within the distal delivery portion 73 of the inner tube 60. The number and arrangement of the exit ports 74 may vary while still allowing a fluid to be expelled therethrough the exit ports 74 as further described below.

The inner tube 60 supports plunger 66 inserted within the inner lumen 68 of the inner tube 60 and providing an elongated circular cylindrical tube extending between a distal end 76 and a proximal end 78 and having a length of at least 10 centimeters and at least 26 centimeters and approximately 26 centimeters to 1 meter long. The plunger 66 may also be oval in cross section.

The plunger 66 may include an outer wall 79 surrounding an inner lumen 80 having a generally constant inner and outer diameter, the outer diameter closely matching the inner diameter of the inner tube 60 to promote fluid flow out of the exit ports of the inner tube 60 primarily between the distal end of the inner tube 60 and the distal end of the plunger 66. In this respect the outer diameter of the outer wall 79 of the plunger 66 may generally range from 1.5 mm to 2.5 mm for example between 5 French and 6 French and able to be inserted within the inner lumen 68 of the inner tube 60. The thickness of the outer wall 79 may be approximately 0.1 mm to 0.5 mm. The outer wall 79 of the plunger 66 may be constructed of a thermoplastic having high temperature resistance, is chemically inert, has a low coefficient of friction, and good biocompatibility. The material may be a fluoropolymer such as polytetrafluoroethylene (PTFE). The outer wall 79 may be a flexible material to allow the plunger 66 to be easily inserted into the inner tube 60.

The distal end 76 of the plunger 66 may be open along axis 26 to allow an immunotherapy or other medical substance 27 to be injected through the inner lumen 80 of the plunger 66 and flow out through the distal end 76 of the plunger 66 into the inner tube 60. The distal end 76 of the plunger 66 may include a radiopaque marker 22 allowing the medical professional to position the distal end 76 of the plunger 66 within the inner tube 60 to a desired location.

Referring to FIG. 4, the inner tube 60 may be inserted through the inner lumen 14 of the outer tube 12 until the distal end 62 of the inner tube 60 is positioned at the desired location representing an outer bound 81 of a fluid delivery area 72 of the catheter assembly 10. The position of the inner tube 60 may be assisted by image guidance such as the radiopaque marker 22 positioned at the distal end 62 of the inner tube 60.

The plunger 66 may then be inserted through the inner lumen 68 of the inner tube 60 until the distal end 76 of the plunger 66 is positioned at the desired location representing an inner bound 82 of the fluid delivery area 72 of the catheter assembly 10. The positioning of the plunger 66 may be assisted by image guidance such as the radiopaque marker 22 positioned at the distal end 76 of the plunger 66.

The immunotherapy or other medical substance 27 may be injected through the inner intratumoral injection catheter 25 by a pump or a syringe 84, for example, a Luer lock syringe. The syringe 84 may be connected to the open proximal end 78 of the plunger 66 and the immunotherapy or other medical substance 27 may be injected through the inner lumen 80 of the plunger 66. A volume of immunotherapy or other medical substance 27 injected into the plunger 66 may be less than 1 mL and may be up to 15 mL and may be up to 100 mL.

The exit ports 74 of the inner tube 60 may communicate with the exit ports 32 of the outer tube 12 to allow immunotherapy or other medical substance 27 to flow from the inner lumen 68 of the inner tube 60 out through the outer tube 12. In one embodiment, the respective exit ports 32, 74 may at least partially overlap facilitating fluid flow through the exit ports 32, 74 against the resistance of the surrounding tissue. In this respect the spacing between the exit ports 32, 74 along the axis 26 may be less than a length of the exit ports 32, 74 along the axis 26 encouraging the overlap of the exit ports 32, 74. In another embodiment, a narrow spacing between the inner tube 60 and the outer tube 12 facilitates fluid flow through the exit ports 32, 74 even when the exit ports 32, 74 are not overlapping.

The outer tube 12 and the inner tube 60 may fit with respect to teach other to restrict backflow of the immunotherapy or other medical substance 27 axially between the outer tube 12 and the inner tube 60. The outer tube 12 an inner tube 60 may also provide a liquid tight seal against the flow of immunotherapy or other medical substance 27 axially between the outer tube 12 and the inner tube 60.

The fluid delivery area 72 extending between the distal end 62 of the inner tube 60 and the distal end 76 of the plunger 66 defines the area of radial delivery of immunotherapy or other medical substance 27 from the catheter assembly 10 to the surrounding tumor site 16. In this respect, the fluid delivery area 72 may be precisely controlled or adjusted to deliver the immunotherapy or other medical substance 27 to a smaller or larger radial area as desired. For example, the fluid delivery area 72 may be between 1 cm and 15 cm along a length of the outer tube 12. The fluid delivery area 72 may also be precisely controlled or adjusted to deliver the immunotherapy or other medical substance 27 at controlled depths along the length of the catheter assembly 10, for example, delivering radiotherapy to deeper, distal locations along the catheter assembly 10 or shallower, proximal locations along the catheter assembly 10 depending on where a tumor or tumors are located.

In an exemplary embodiment, shown in FIG. 4, the catheter assembly 10 may initially deliver immunotherapy or other medical substance 27 to a smaller tumor using a smaller fluid delivery area 72 at a more distal location along the catheter assembly 10 and subsequently deliver immunotherapy or other medical substance 27 to a larger tumor using a larger fluid delivery area 72 at a more proximal location along the catheter assembly 10. In another exemplary embodiment, as illustrated in FIG. 2, the catheter assembly 10 may deliver immunotherapy or other medical substance 27 to multiple locations or zones within a single tumor by precise placement of the fluid delivery area 72 along a length of the catheter assembly 10 correlating with a first and second position with respect to the tumor.

After delivery of the immunotherapy or other medical substance 27 through the catheter assembly 10 is complete, the catheter assembly 10 may be withdrawn from the body completing the brachytherapy and intratumoral injection combined treatment.

Referring to FIG. 5, in an alternative embodiment of the present invention, the inner intratumoral injection catheter 25 may be an elongated circular cylindrical inner tube 60 extending along an axis 26 between a distal end 62 terminating within the outer tube 12, and a proximal end 64 receiving an inner plunger 66. The inner tube 60 may have an outer diameter that is less than 3.5 mm and less than 3 mm and between 3 and 3.5 mm. The inner tube 60 may include an inner tube wall 61 surrounding an inner lumen 68 having a generally constant inner and outer diameter. The inner tube 60 diameter may be reduced in some embodiments, for example, less than 3 mm or less than 2.5 mm or less than 2 mm, to minimize the waste of any liquid remaining in the inner tube 60 after plunger application and to accurately enable injection of small liquid volumes into the tumor site 16.

The distal end 62 of the inner tube 60 receives an end cap 90, snugly fitting over an end of the inner tube wall 61 of the inner tube 60 and closing the distal end 62 of the inner tube 60 by an end wall 92 from fluid flowing distally outward from the inner tube 60 along the axis 26.

The end cap 90 further includes one or more inlet/exit ports 94 extending laterally, perpendicular to the axis 26, through an outer wall of the end cap 90 to allow fluid flow from the inner lumen 68 of the inner tube 60 outward into the end cap 90 and through the inlet/exit ports 94. The inlet/exit ports 94 of the end cap 90 may be circular holes, although other shapes such as elongated slots are contemplated. The inlet/exit ports 94 may be less than 3 mm in diameter and less than 2 mm in diameter and approximately 0.5 to 1.5 mm and about 1 mm in diameter.

The inlet/exit ports 94 may be spaced in equal separation about a circumference of the inner tube 60. In one embodiment, four inlet/exit ports 94 may be spaced evenly at 90-degree intervals about a circumference of the inner tube 60. The inlet/exit ports 94 may be separated by a distance that is approximately 1 mm to 2 mm about the circumference of the inner tube 60. The distance between inlet/exit ports 94 may be less than a diameter of the inlet/exit ports 94. It is contemplated that any number of inlet/exit ports 94 may be arranged about the circumference of the outer tube 12 such as one, two, or three inlet/exit ports 94. The inlet/exit ports 94 may be designed to enable a removal of air from the inner tube 60 prior to injection and to further minimize leakage along the longitudinal axis 26 of the catheter between the outer tube 12 and the inner tube 60. The controlled delivery and minimized amount of injected materials from the inlet/exit ports 94 also reduces the amount of excess liquid injected into the tumor site 16 thus minimizing the excess liquid material leaking out of the tumor site 16.

The inner plunger 66 received within the inner tube 60 may include a plunger shaft 100 having a proximal end 102 extending away from the proximal end 64 of the inner tube 60 and a distal end 104 extending within the inner tube 60. The distal end 104 of the plunger shaft 100 may be connected to a plunger piston 106, for example, being an elastomeric material such as rubber or a polymer, and fitting snugly within the volume of the inner tube 60.

The proximal end 102 of the plunger shaft 100 may provide for a thumb button 108 for manual operation by a medical professional who may press on the thumb button 108 with a thumb while having index and middle fingers respectively stabilized by outwardly extending grip flanges 110, 112 respectively extending outwardly from the proximal end 64 of the inner tube 60 at opposed ends of a diameter of the inner tube 60. In this way the medical professional through manual pressure by the thumb on an end of the inner plunger 66, may manually operate the inner plunger 66 to move the plunger piston through the inner tube 60.

As shown in FIG. 5, in a medical fluid loading step, the medical professional pulls the inner plunger 66 out from the inner tube 60 along direction 116 to move the plunger piston 106 away from the distal end 62 of the inner tube 60 causing the inner tube 60 to fill with the immunotherapy or other medical substance 27 through the inlet/exit ports 94. Conversely, the medical professional pushes on the thumb button 108 of the inner plunger 66 in an opposite direction 118 (FIG. 6) to move the plunger piston 106 towards the distal end 62 of the inner tube 60 causing the discharge of the immunotherapy or other medical substance 27 from the inner tube 60 through the inlet/exit ports 94.

Figure 6:
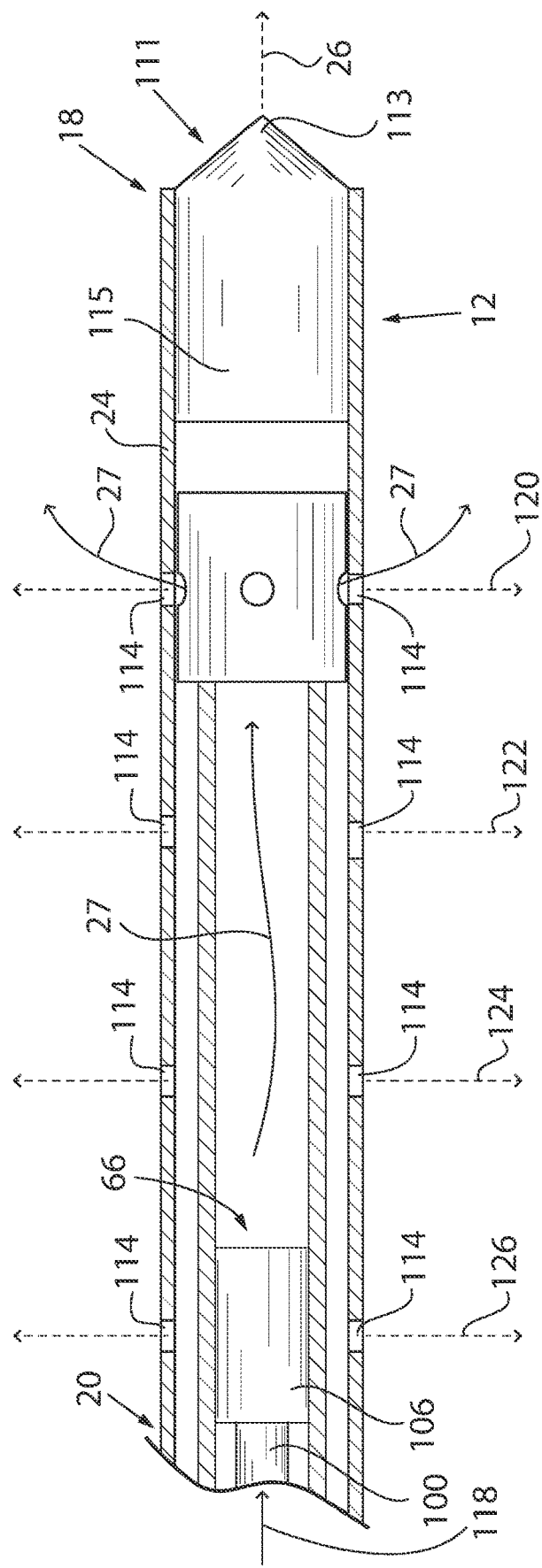
FIG. 6 is a cross-sectional view of the intratumoral injection catheter of FIG. 5 installed within an alternative embodiment of the needle outer tube showing the inlet/outlet ports of the inner tube being aligned with the exit ports of the outer tube, and the plunger of the intratumoral injection catheter being pushed inwardly along the inner tube to expel the fluid from the intratumoral injection catheter through the ports of the inner tube and the outer tube.

Referring now to FIG. 6, in the alternative embodiment of the present invention, the outer tube 12 may be an elongated circular cylindrical tube extending between a distal end 18 and a proximal end 20 along the axis 26. The outer tube 12 may have an outer diameter of less than 4 mm and less than 3.6 mm and between 3 and 4 mm. The outer tube 12 may include an outer tube wall 24 surrounding an inner lumen 14 having a generally constant inner and outer diameter.

The inner intratumoral injection catheter 25 may have an outer diameter closely matching the inner diameter of the outer tube 12 to be inserted into the outer tube 12 while restricting fluid flow axially between the outer tube 12 and the inner tube 60 as previously described above with respect to FIGS. 1 and 2.

The distal end 18 of the outer tube wall 24 extending into the tumor site 16 may receive a hard, rigid, pointed needle 111 extending distally along the axis 26 from within the outer tube wall 24 and having a stud 115 received by the inner lumen 14 of the outer tube wall 24 opening axially at the distal end 18. The stud 115 may be generally cylindrical and have the same outer diameter as the inner diameter of the outer tube 12 to fit tightly therein the outer tube wall 24. The stud 115 may extend at least 20 mm and at least 25 mm and approximately 25 mm to 40 mm in length within the inner lumen 14 in order to provide additional stiffness to the flexible outer tube 12. The needle 111 tapers to a sharp point 113 generally aligned with the axis 26 and able to penetrate or puncture a patient's skin. The needle 111 may be made out of a metal such as stainless steel providing a stiffening distal end 18 to the otherwise flexible outer tube wall 24.

A section of the outer tube 12 proximal to the needle 111 is used to deliver immunotherapy or other medical substance 27 circumferentially at multiple depths of the tumor site 16 along axis 26 and includes one or more exit ports 114 extending through the outer tube wall 24, and spaced in generally equal separation about a circumference of the outer tube 12 to form rings of holes along the outer tube 12, and spaced in generally equal separation along a length of the outer tube 12 along axis 26.

In one embodiment, four exit ports 114 may be spaced equally at 90-degree intervals about a circumference of the outer tube 12. The exit ports 114 may be separated by a distance of approximately 1 mm to 2 mm about the circumference of the outer tube 12. The distance between exit ports 114 may be less than a diameter of the exit ports 114. It contemplated that any number of exit ports 114 may be arranged about the circumference of the outer tube 12 such as one, two or three exit ports 114.

The exit ports 114 may be separated by a distance along axis 26 that is less than 15 mm apart and less than 10 mm apart and approximately 5 mm to 10 mm apart and about 9 mm apart. The exit ports 114 may be spaced apart a distance that is less than an average length of a tumor. In one embodiment, the exit ports 114 are spaced apart along the axis 26 at at least four longitudinal locations and between four and ten longitudinal locations for a total of at least eight or at least sixteen exit ports 114 distributed within the outer tube 12.

The exit ports 114 may be circular holes, although other shapes such as elongated slots or other shaped holes are contemplated. The exit ports 114 may be less than 3 mm in diameter and less than 2 mm in diameter and approximately 0.5 to 1.5 mm and about 1 mm in diameter.

In operation, the outer tube 12 may be positioned such that one or more of the exit ports 114 along axis 26 are aligned with respect to the desired tumor site 16. The alignment of the exit ports 114 of the outer tube 12 with the tumor site 16 may be facilitated by alignment indicators such as radiopaque markers at the distal end 18 of the outer tube 12 as previously described above.

An inner brachytherapy insertion catheter 23 may be inserted into the inner lumen 14 of the outer tube 12 until the radioactive seed 40 is positioned at a desired location with respect to the tumor site 16. The inner brachytherapy insertion catheter 23 may be a standard brachytherapy needle, for example, a Brachystar needle manufactured by Bard, consisting of a hollow outer tube 12 and removable inner stylet. After the outer tube 12 is installed at the proper location within the patient, the seed 40 may be deposited by removing the stylet from the outer tube 12. Then the seed 40 is inserted through the outer tube 12. The inner brachytherapy insertion catheter 23 may then be withdrawn from the outer tube 12 once the radiation therapy is complete.

The inner intratumoral injection catheter 25 may be preloaded with immunotherapy or other medical substance 27 by pulling the inner plunger 66 out from the inner tube 60 along direction 116 to draw in the liquid, as previously described above with respect to FIG. 5.

The inner tube 60 is then inserted into the inner lumen 14 of the outer tube 12 until the inlet/exit ports 94 of the end cap 90 of the inner tube 60 are aligned with a first axial position 120 along the axis 26 corresponding with a ring of exit ports 114 closest to the distal end 18 of the outer tube 12. The first axial position 120 may correspond with a desired depth for immunotherapy or other medical substance 27 delivery. A second axial position 122, third axial position 124, and fourth axial position 126 along axis 26 may correspond with the other longitudinal positions of the rings of exit ports 114 as one moves from the distal end 18 of the outer tube 12 towards the proximal end 20 of the outer tube 12, and representing other possible depths for immunotherapy or other medical substance 27 delivery. It is understood that the inlet/exit ports 94 of the end cap 90 of the inner tube 60 may be slidably aligned at any of the axial positions 120, 122, 124, 126 while the exit ports 114 and the outer tube 12 remain stationary within the patient's body. The alignment of the inlet/exit ports 94 and the exit ports 114 may be facilitated by alignment indicators such as radiopaque markers indicating a longitudinal position of the exit ports 114 of the outer tube 12 and a longitudinal position of the inlet/exit ports 94 of the inner tube 60 along axis 26.

The inner tube 60 may be torqued or rotated about the axis 26 so that the inlet/exit ports 94 are also circumferentially aligned with the exit ports 114 of the outer tube 12 such that the respective holes of the inlet/exit ports 94 and the exit ports 114 overlap or are substantially aligned or concentric with each other. Again, the alignment of the inlet/exit ports 94 and the exit ports 114 may be facilitated by alignment indicators such as radiopaque markers indicating a circumferential position of the exit ports 114 of the outer tube 12 and a circumferential position of the inlet/exit ports 94 of the inner tube 60 about axis 26. It is understood that in some situations, there may be a gap between the inner tube 60 and the outer tube 12 to allow the immunotherapy or other medical substance 27 to be expelled through the inlet/exit ports 94 and exit ports 114 even if the inlet/exit ports 94 and the exit ports 114 are not overlapping, aligned or concentric with each other.

The medical professional may push on the thumb button 108 of the inner plunger 66 in the direction 118 to move the plunger piston 106 towards the distal end 62 of the inner tube 60 causing the discharge of the immunotherapy or other medical substance 27 from the inner tube 60 outward through the inlet/exit ports 94 of the end cap 90 and further exiting the exit ports 114 of the outer tube 12 to deliver immunotherapy or other medical substance 27 to the tumor site 16 as similarly described above with respect to the first embodiment of the invention.

After delivery of the immunotherapy or other medical substance 27 through the catheter assembly 10 is complete, the catheter assembly 10 may be withdrawn from the body completing the brachytherapy and intratumoral injection combined treatment.

Brachytherapy has been used for treatments of cancers of the prostate, breast, gynecologic organs, pituitary, brain, external auditory canal, upper gum, tongue, ethmoid sinus, stomal recurrences of laryngeal tumors, and for sarcomas and tumors at other sites of the head and neck, spine, liver, colorectum, and extremity, among other potential applications. It is understood that during brachytherapy anywhere between one and 100 separate catheter assemblies 10 may be implanted into or placed alongside the tumor site 16 simultaneously. In an alternative embodiment of the present invention the catheter assembly 10 may be a multi-lumen balloon catheter allowing for multiple outer tubes 12 and multiple inner brachytherapy insertion catheters 23 to be inserted therein and expanded into a balloon shape in order to deliver the radiotherapy to a three dimensional tumor site or surgical cavity 16, for example, where a tumor has been removed.

It is also understood that the catheter assembly 10 of the present invention may be used in connection with other drug delivery therapies to a tumor site such as chemotherapy.

In one embodiment of the present invention, the catheter assembly 10 may be used in connection with the delivery of 1) cytotoxic chemotherapies or 2) molecular targeted agents. The delivery of 1) cytotoxic chemotherapies or 2) molecular targeted agents may radiosensitize or otherwise enhance local tumor control together with brachytherapy.

In one embodiment of the present invention, the catheter assembly 10 may be used in connection with the delivery of oncolytic virus therapies that may activate anti-tumor immunity in combination with brachytherapy but cannot be given with safety and efficacy by other routes.

In one embodiment of the present invention, the catheter assembly 10 may be used in connection with the delivery of cell therapies (e.g. CAR-T cells, CAR-NK cells) that may have greater antitumor effect in combo with brachytherapy but which do not adequately reach the tumor site unless given intratumorally.

In one embodiment of the present invention, the catheter assembly 10 may be used in connection with the delivery of marking agents (e.g., tattoo ink) or contrast agents for radiological imaging when either might be needed in combination with brachytherapy Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

What we claim is:

1. A catheter assembly for delivery of a medical solution inside a human body comprising:
    an outer tube having a wall surrounding a central lumen extending along an axis and including at least one exit port positioned along its length extending through the wall and having an open proximal end;
    an inner tube having a wall surrounding a central lumen extending along the axis and slidably receivable within the central lumen of the outer tube along the axis at the proximal end of the outer tube and having a closed distal end and having at least one exit port extending through the wall and communicating with the at least one exit port of the outer tube to allow fluid flow from the central lumen of the inner tube through the at least one exit port of the inner tube and the at least one exit port of the outer tube at a range of relative positions along the axis; and
    an inner plunger slidably receivable within the central lumen of the inner tube along the axis at the proximal end of the inner tube, the plunger interfacing with the inner tube to promote fluid flow into and out of the at least one exit port of the inner tube by translating the plunger along the axis;
    wherein the inner plunger is configured to drive fluid flow into the central lumen of the inner tube through the at least one exit port of the inner tube by translation of the inner plunger in a first direction along the axis and to drive fluid flow out of the central lumen of the inner tube through the at least one exit port of the inner tube and the at least one exit port of the outer tube by translation of the inner plunger in a second opposite direction along the axis.

2. The assembly of claim 1 wherein the at least one exit port of the outer tube is multiple exit ports distributed evenly along a length of the outer tube.

3. The assembly of claim 2 wherein the multiple exit ports are separated by a distance that is less than 10 mm apart along the length of the outer tube.

4. The assembly of claim 1 wherein the at least one exit port of the outer tube is multiple exit ports distributed about a circumference of the outer tube.

5. The assembly of claim 4 wherein the at least one exit port of the inner tube is multiple exit ports distributed about a circumference of the inner tube.

6. The assembly of claim 5 wherein the multiple exit ports of the outer tube and inner tube are separated by a distance that is less than 5 mm apart about a circumference of the outer tube and inner tube, respectively.

7. The assembly of claim 1 wherein the at least one exit port of the inner tube and the at least one exit port of the outer tube are circular.

8. The assembly of claim 1 wherein the outer tube and inner tube fit to restrict fluid flow axially between the outer tube and the inner tube.

9. The assembly of claim 8 wherein the outer tube and inner tube provide a liquid tight seal against fluid flow axially between the outer tube and the inner tube.

10. The assembly of claim 1 where the outer tube and inner tube are substantially cylindrical.

11. The assembly of claim 1 wherein the outer tube and inner tube are flexible.

12. The assembly of claim 11 wherein the outer tube and inner tube are constructed of a polytetrafluoroethylene fluoropolymer.

13. The assembly of claim 1 wherein the outer tube has a closed distal end converging to a tapered point.

14. The assembly of claim 1 further comprising at least one radiopaque marker indicating a position of the closed distal end of the inner tube and at least one radiopaque marker indicating a position of a closed distal end of the inner plunger with respect to the inner tube.

15. A catheter assembly comprising:
- an outer tube having a wall surrounding a central lumen extending along an axis and including at least one exit port positioned along its length extending through the wall and having an open proximal end;
- an inner tube having a wall surrounding a central lumen extending along the axis and slidably receivable within the central lumen of the outer tube along the axis at the proximal end of the outer tube and having a closed distal end and having at least one exit port extending through the wall and communicating with the at least one exit port of the outer tube to allow fluid flow from the central lumen of the inner tube through the at least one exit port of the inner tube and the at least one exit port of the outer tube at a range of relative positions along the axis;
- an inner plunger slidably receivable within the central lumen of the inner tube along the axis at the proximal end of the inner tube, the plunger interfacing with the inner tube to promote fluid flow into and out of the at least one exit port of the inner tube by translating the plunger along the axis; and
- a brachytherapy insertion catheter slidably fitting within the outer tube.

16. The assembly of claim 15 wherein a lumen of the brachytherapy insertion catheter is sized to receive radiotherapy seeds guided therealong.

* * * * *